United States Patent [19]

Matsumoto et al.

[11] Patent Number: 5,008,387

[45] Date of Patent: Apr. 16, 1991

[54] PROCESS FOR PURIFYING SUCROSE FATTY ACID ESTERS

[75] Inventors: Shusaku Matsumoto, Kyoto; Yoshio Hatakawa, Higashiosaka; Akihiko Nakajima, Kyoto, all of Japan

[73] Assignee: Dai-Ichi Kogyo Seiyaku Co., Ltd., Kyoto, Japan

[21] Appl. No.: 338,012

[22] Filed: Apr. 14, 1989

[30] Foreign Application Priority Data

Apr. 18, 1988 [JP] Japan ................................. 63-95243

[51] Int. Cl.$^5$ ...................... C07H 1/00; C07H 13/00; C13F 3/00
[52] U.S. Cl. .................................. 536/119; 536/127; 536/124; 536/120; 536/115
[58] Field of Search ............... 536/127, 124, 119, 115, 536/120

[56] References Cited

U.S. PATENT DOCUMENTS

| T 995,002 | 6/1980 | Zeringue, Jr. et al. | 536/119 |
| 3,748,324 | 7/1973 | Mizutani et al. | 536/119 |
| 3,792,041 | 8/1970 | Yamagishi et al. | 536/119 |
| 4,252,834 | 2/1981 | Inamine et al. | 426/103 |

FOREIGN PATENT DOCUMENTS

| 42-11568 | 6/1967 | Japan . |
| 48-10448 | 4/1973 | Japan . |
| 809815 | 3/1959 | United Kingdom . |

*Primary Examiner*—Ronald W. Griffin
*Assistant Examiner*—Everett White
*Attorney, Agent, or Firm*—Armstrong, Nikaido, Marmelstein, Kubovcik & Murray

[57] ABSTRACT

From a reaction mixture obtained by reaction of sucrose and a fatty acid alkyl ester in the presence of a catalyst, a purified sucrose fatty acid ester is prepared without using organic solvents for purification by adding water to the reaction mixture and subjecting the resulting aqueous solution to ultrafiltration, thereby removing the unreacted sucrose, the catalyst or a salt derived from the catalyst, and the volatile component used as the reaction medium together with water. A powder of the purified sucrose fatty acid ester is easily, economically and safely prepared by subjecting the aqueous solution remaining in the ultrafiltration to reverse osmosis and spray-drying the resulting concentrate.

19 Claims, No Drawings

PROCESS FOR PURIFYING SUCROSE FATTY ACID ESTERS

BACKGROUND OF THE INVENTION

The present invention relates to a process for purifying a sucrose fatty acid ester (sugar ester). More particularly, the present invention relates to a treatment of a reaction mixture containing a sucrose fatty acid ester to remove the unreacted sucrose, a salt by-produced by neutralization of a catalyst used in the production of the sucrose fatty acid ester, and a volatile component on an industrial scale, and relates to a recovery of the purified sucrose fatty acid ester in the form of a powder.

Sucrose fatty acid esters (sugar esters) useful as surface active agents are prepared industrially at present by either a solvent process wherein sucrose is reacted with a methyl ester of a higher fatty acid having 8 to 22 carbon atoms in the presence of a suitable catalyst in an organic solvent such as dimethylformamide or dimethylsulfoxide, as disclosed in Japanese Patent Publication Kokoku No. 35-13102; or an aqueous medium process wherein sucrose is formed into a molten mixture with a fatty acid salt (soap) using water without using an organic solvent, and is then reacted with a higher fatty acid methyl ester in the presence of a catalyst, as disclosed in Japanese Patent Publication Kokoku No. 51-14485. However, even according to any of these processes, the obtained reaction mixture contains impurities such as the unreacted sucrose, the unreacted fatty acid methyl ester, residual catalyst, soap, free fatty acid, volatile material, etc. in addition to the desired sucrose fatty acid ester. These impurities, at least impurities whose contents exceed the specified amounts must be removed prior to being put on the market. In particular, removal of the unreacted sucrose is very important because of inclusion in a large amount.

The removal of the unreacted sucrose from the reaction mixture containing sucrose fatty acid ester has been generally conducted by utilizing the property that sucrose is slightly soluble in common organic solvents, namely by adding a solvent to the reaction mixture to precipitate the unreacted sucrose and removing the precipitate. This process may be useful for the production on a small scale, but is not suitable for the production on an industrial scale because of problems in handling the solvent, such as labor and time for recovering the solvent, risk of a fire, and environmental sanitation for workers. However, since there is no other useful means, organic solvents have been still used for removal of the unreacted sucrose and other impurities. For example, in Japanese Patent Pulication Kokoku No. 42-11568 and No. 48-10448, it is disclosed that organic solvents such as butyl alcohol, toluene, methyl ethyl ketone and ethyl acetate are effective for purification including removal of the unreacted sucrose. The use of organic solvents is accompanied, for example, by the following disadvantages: (1) risk of explosion and fire, (2) provision of explosion and fire prevention means to electric devices, (3) application of closed system to production equipment for explosion and fire prevention, (4) requirement of fireproof construction for entire building by way of precaution against explosion and fire, (5) rise in fixed cost due to the items (2), (3) and (4), (6) rise in materials cost due to loss of solvent, (7) contamination of the product with remaining solvent, and (8) adverse influence on health of workers, and increase of process steps and cost resulting therefrom.

In view of these circumstances, it has been desired to develop a technique capable of removing the unreacted sucrose and other impurities from the crude reaction mixture without using organic solvents.

Accordingly, it is a primary object of the present invention to establish a technique for simultaneously removing not only the unreacted sucrose, but also the remaining catalyst, salts which is the by-product, of a, volatile components (namely remaining solvents used in the reaction for the production of sucrose fatty acid ester) and other impurities from the crude reaction mixture without using organic solvents.

A further object of the present invention is to provide a process for recovering a sucrose fatty acid ester without using organic solvents from a reaction mixture obtained by the reaction of sucrose and a fatty acid ester according to the organic solvent process or the aqueous medium process.

Another object of the invention is to provide a process for recovering a purified sucrose fatty acid ester in the form of a powder without using orgnaic solvents in purification of the ester.

These and other objects of the present invention will become apparent from the description hereinafter.

SUMMARY OF THE INVENTION

In accordance with the present invention, there is provided a process for treating a reaction mixture containing a sucrose fatty acid ester produced by the reaction of sucrose and a fatty acid alkyl ester in the presence of a catalyst, which comprises subjecting to ultrafiltration an aqueous solution of a sucrose fatty acid ester containing the unreacted sucrose, the unreacted fatty acid alkyl ester, the catalyst, a soap, a fatty acid and a volatile component.

It is known that in water the sucrose fatty acid ester molecules aggregate with each other to form high molecular weight micelles under certain conditions.

The sucrose fatty acid esters include for instance a monoester, diester and triester wherein 1 to 3 fatty acid residues are attached to any of oxygen atoms of the 8 hydroxyl groups of sucrose molecule. As is well known, since the monoester is low in ability to form micelles in water while having a larger hydrophilic property than diester and triester, it forms a relatively low weight micelle (in other words, a micelle having a small diameter). In contrast, the diester and triester have a very large micelle forming ability while being relatively low in hydrophilic property and, therefore, they form micelles of very large weight (namely large micellar diameter). It is seldom that the sucrose fatty acid ester is produced and put on the market in the form of monoester alone. Commerially available sucrose fatty acid esters are usually those produced in the form of a mixture having a monoester content of 70%, 50%, 30% or the like.

According to investigation of the present inventors, since the sucrose fatty acid ester having a high monoester content, for instance, as high as 70%, forms micelles of a lower weight in comparison to the sucrose fatty acid ester having a monoester content as low as 50%, the microscopic diameter of micelle is small as such and it is easy to pass through a ultrafiltration membrane having a specified pore diameter in comparison with the sucrose fatty acid ester having a monoester content of 50% and, therefore, the sucrose fatty acid ester having a high monoester content has an undesirable tendency to pass through the membrane together with the unreacted sucrose, a salt derived from a catalyst by neutralization of the catalyst with an acid, and a volatile component. Such a problem can be easily eliminated by selecting the ultrafiltration membrane, and it is convenient for enhancing the treating speed to select the membrane having a low fractionating molecular weight (namely small pore diameter) when desired to remove the unreacted sucrose, salt derived from the catalyst and volatile component from the sucrose ester having a high monoester content, and to select the membrane having a large fractionating molecular weight (namely large pore diameter) for the sucrose ester having a low monoester content.

It is confirmed by the present inventors that it is practically impossible to separate the unreacted fatty acid ester such as fatty acid methyl ester, soap and fatty acid among substances included in the reaction mixture from the sucrose ester by a filtration means because they are present in the state of being included in the micelles of the sucrose ester. In other words, impurities permeable to a filtration membrane having an appropriate fractionating molecular weight together with water by a pressure as actuating force are the unreacted sucrose, a salt derived from the catalyst and a volatile component (polar materials having a high water-solubility and a high affinity to sucrose which have been used as solvents in synthesis of sucrose fatty acid ester, e.g. dimethylsulfoxide and dimethylformamide), while the unreacted fatty acid ester, soap and free fatty acid are entrapped in the sucrose ester micelles and they are impermeable to the filtration membrane.

Thus, by skillfully utilizing these facts and by selecting a filtration membrane having an appropriate fractionation molecular weight, the present inventors have succeeded in separating and removing unreacted sucrose, salt derived from the catalyst and volatile component from other components, namely sucrose fatty acid ester, unreacted fatty acid ester, soap and fatty acid.

In another aspect of the present invention, the aqueous solution obtained by the ultrafiltration of a mixture containing the sucrose fatty acid ester, unreacted fatty acid ester, soap and fatty acid is then brought into contact with a reverse osmosis membrane under pressure, and if necessary, is further concentrated by evaporating water, and the resulting slurry having an appropriate solid concentration is spray-dried to give a powder.

DETAILED DESCRIPTION

The present invention is applicable to any of the crude reaction mixtures obtained in known processes for the preparation of sucrose fatty acid esters by interesterification reaction of sucrose and a fatty acid alkyl ester using an organic solvent. In general, methyl esters of higher fatty acids having 8 to 22 carbon atoms have been used as the fatty acid alkyl ester in the preparation of the sucrose esters.

The term "volatile component" as used herein means an organic solvent used as the reaction medium in the preparation of the sucrose fatty acid esters.

In order to select a ultrafiltration membrane having an adequate fractionating molecular weight, it is necessary to previously know approximate molecular weights of the subject substances. The molecular weights of typical single compounds involved in the present invention are as follows:

(1) Sucrose = 342
(2) Unreacted fatty acid methyl ester
  Methyl stearate = 290
(3) Salt produced by neutralization of catalyst ($K_2CO_3$)
  In case of lactic acid: potassium lactate = 128
  In caser of acetic acid: potassium acetate = 98
(4) Volatile component
  Dimethylsulfoxide = 78
  Dimethylformamide = 73
(5) Sucrose fatty acid ester (single compound not forming micelle)
  Sucrose monostearate = 600
  Sucrose distearate = 858
  Sucrose tristearate = 1116
  Other sucrose fatty acid esters such as myristate, palmitate, arachate and behenate have also similar molecular weight to the above molecular weights.
(6) Soap
  Sodium stearate = 298
  Potassium stearate = 314
(7) Fatty acid
  Stearic acid = 276
(8) Water = 18

The apparent molecular weight of a sucrose fatty acid ester micelle can be experimentally estimated as follows:

The sucrose fatty acid ester in a practical aqueous solution forms micelles in water. Therefore, if 10 molecules associate per micelle, the apparent molecular weight of the micelle is:

molecular weight of monoester $(600) \times 10 = 6{,}000$ (regarded as 100% monoester), molecular weight of diester $(858) \times 10 = 8{,}580$ (regarded as 100% diester), and molecular weight of triester $(1{,}116) \times 10 = 11{,}160$ (regarded as 100% triester).

Since the actual sucrose fatty acid ester is a mixture composed mainly of mono-, di- and triesters, the apparent molecular weight of a micelle of a sucrose fatty acid ester is defined as the average value thereof.

The selection of a membrane for ultrafiltration adequate for the purposes of the present invention is conducted as follows:

In case of a ultrafiltration membrane having a fractionating molecular weight of 200, even if it is attempted to remove the unreacted sucrose, a salt resulting from a catalyst such as $K_2CO_3$ and a volatile component (organic solvent) while feeding a reaction mixture in the form of an aqueous solution with applying a pressure, the components separable by such a membrane are only water, the salt and the organic solvent which have lower molecular weights than the fractionating molecular weight 200 of the membrane. Since only sucrose which has a molecular weight of 342 larger than the fractionating molecular weight 200, is impermeable to the membrane, it cannot be separated from the sucrose fatty acid ester.

In case of a ultrafiltration membrane having a fractionating molecular weight of 5,000, sucrose, salt derived from catalyst and volatile component can easily pass through fine pores of the membrane, since they have a molecular weight less than 5,000. The sucrose fatty acid ester forms micelles as mentioned above. The sucrose ester is estimated to have an apparent molecular weight of 6,000 or more on the assumption that the number of sucrose ester molecules associated is 10 or more. Therefore, the micelles would not be permeable to the membrane having a fractionating molecular weight of 5,000. Since the apparent molecular weight of the micelle would be in fact more than 6,000, a membrane having a fractionating molecular weight of more than 5,000 can be used and this is experimentally confirmed by the present inventors.

Investigation has been made also with respect to a membrane having a fractionating molecular weight of 1,000. The results are as expected, and such a membrane can be used in the present invention.

The ultrafiltration membrane is selected from those having a fractionating molecular weight of 1,000 or more in view of the size or weight of micelles of the sucrose fatty acid esters, treatment efficiency and other conditions. According to the present invention, by suitably selecting the fractionating molecular weight of the ultrafiltration membrane, it is possible to efficiently remove impurities including the unreacted sucrose included in the reaction mixture in the preparation of sucrose fatty acid esters.

The ultrafiltration membrane should also satisfy the following conditions.

(1) It has a resistance to a physical external force.
(2) It has a thermal resistance, and is not decomposed by microorganisms.
(3) It has an appropriate fractionating molecular weight and has a large treating ability.
(4) The working life is long.
(5) It is available with an economical cost.

The advance of technique of the preparation of ultrafiltration membrane in recent years is marked, and therefore the membranes satisfying the above conditions are available also from those put on the market.

The reaction mixtures obtained by interesterification between sucrose and a fatty acid methyl ester to prepare a sucrose fatty acid ester usually contain, in addition to the objective sucrose fatty acid ester, the unreacted sucrose, the unreacted fatty acid methyl ester and other impurities such as the remaining catalyst (e.g. $K_2CO_3$), a soap (fatty acid salt), a fatty acid and a volatile component (organic solvent used as the medium in the reaction, e.g. dimethylsulfoxide or dimethylformamide). A mixture containing 15 to 95% by weight of sucrose fatty acid ester, 1 to 80% by weight of unreacted sucrose, 0.5 to 10% by weight of unreacted fatty acid methyl ester, 0.05 to 7% by weight of catalyst such as $K_2CO_3$, 1 to 60% by weight of soap, 0.5 to 10% by weight of fatty acid and 0 to 50% by weight of volatile component is suitable for the purification according to the present invention. With respect to the fatty acid portion in the product and the impurities, saturation or unsaturation does not matter so long as the fatty acid methyl ester included in the reaction mixture is methyl esters of fatty acids having 8 to 22 carbon atoms and the sucrose fatty acid esters derived therefrom are those having a softening point or melting point of 47° C. or higher.

Potassium carbonate is a representative catalyst used in the preparation of sucrose fatty acid esters, but the process of the present invention is of course applicable to the reaction mixtures containing other materials used as the catalyst, e.g. materials known as the catalyst for general alcoholysis such as sodium carbonate and a sodium alkoxide.

The soap and fatty acid included in the reaction mixture are usually those corresponding to the above-mentioned fatty acid methyl ester.

The volatile component is usually dimethylsulfoxide or dimethylformamide used as the organic solvent in the preparation of sucrose fatty acid esters.

A part or all of the organic solvents may be distilled away prior to the purification according to the present invention.

Upon conducting the purification according to the process of the invention, water, preferably deionized water, is added to the reaction mixture to dissolve the contents of the reaction mixture in a water/reaction mixture ratio of 5/1 to 40/1 by weight, preferably 20/1 by weight. Since the sucrose fatty acid ester is subject to hydrolysis under an alkaline condition, the reaction mixture is preferably adjusted to a pH of 6.2 to 8.2, preferably a pH in the vicinity of 7.5 in order to prevent the hydrolysis, by adding an acid to neutralize the catalyst ($K_2CO_3$) prior to the addition of water. The acid used for the neutralization includes an organic acid such as lactic acid or acetic acid and an inorganic acid such as hydrochloric acid or sulfuric acid. When the pH is more than 8.2, the hydrolysis of the sucrose ester is often observed. When the pH is less than 6.2, micelles of the sucrose ester are difficult to form, thus resulting in loss of the sucrose ester due to flowing out outside the system through filtration membrane.

The thus prepared aqueous solution is kept at a temperature of not higher than 80° C. during the ultrafiltration regardless of the kind of the fatty acid methyl ester. When the temperature of the aqueous solution exceeds 80° C., the sucrose ester may be decomposed. In particular, the highest filtration velocity is obtained when the temperature of the aqueous solution to be filtered falls within the range of 40° to 60° C. That is to say, the unreacted sucrose, a salt derived from the catalyst such as $K_2CO_3$ by neutralization with an acid, and the volatile component such as dimethylsulfoxide or dimethylformamide pass the most efficiently through the filtration membrane with water, when the filtration temperature is kept at 40° to 60° C., especially in the vicinity of 50° C. The reason is considered that as a result that the sucrose ester forms huge micelles at a temperature of 40° to 60° C., the total number of micelles decreases and substances which do not take part in micelle formation, such as the unreacted sucrose, become hard to subject to a resistance of the sucrose ester present, thus these substances become easy to move and pass through the membrane.

The aqueous solution prepared from the reaction mixture containing the sucrose fatty acid ester and maintained at a temperature of 40° to 60° C. is brought into contact with a ultrafiltration membrane at a hydrogen ion concentration corresponding to a pH of 6.2 to 8.2 under a pressure of 1 to 20 kg/cm$^2$G applied as actuation source for ultrafiltration by a pump.

As stated before, it is important to determine the fractionating molecular weight of filtration membrane so that the unreacted sucrose and other impurities can be separated efficiently without leakage of the sucrose ester at a high filtration velocity. The present inventors have found that membranes having a fractionating molecular weight of 1,000 to 100,000 are suitable for the purposes of the present invention, whereby the purification can be carried out without impairing the separability of the unreacted sucrose, salt and volatile component at a high filtration velocity, and particularly membranes having a fractionating molecular weight of about 5,000 is the most suitable for the treatment on an industrial scale. The filtration velocity decreases with decreasing the fractionating molecular weight. On the other hand, when the fractionating molecular weight is high, namely within a range exceeding 5,000 and up to 100,000, the sucrose ester may leak. However, such a leakage is slight even if occurs, and is not economically detrimental.

Cellulose membranes are not much preferred in practical use, since they are weak against a physical force and are easily attacked with microorganisms. Polysulfone and polyvinylidene fluoride membranes reinforced by a support layer are suitable in practical use, and these filtration membranes are commercially available. They have excellent thermal, acid and alkali resistances and can withstand a physical external force, and moreover microorganisms do not propagate on the membrane surface. Representative examples of commercially available ultrafiltration membranes suitable for the process of the present invention are, for instance, polyvinylidene fluoride membrane (trade mark "TERP-E-5") and polysulfone membranes (trade mark "TERP-HF-10" and "TERP-HF-100") which are sold by Toray Engineering Kabushiki Kaisha.

According to experiments made by the present inventors using the ultrafiltration membrane "TERP-HF-10" (fractionation molecular weight: 10,000) and an aqueous solution of pH 7.5 prepared from a reaction mixture in the preparation of sucrose fatty acid ester, the separation velocity of the unreacted sucrose reached 4.7 kg/hour at 50° C. and 5.0 kg/cm$^2$G when the effective area of the membrane (per unit) was 8 m$^2$ and the aqueous solution had the composition shown in Table 1. This separation velocity is industrially satisfactory. The separation velocities of a salt derived from the catalyst and the volatile component were also sufficiently high. Since the rate of removal of the unreacted sucrose, salt and volatile component can be raised to a satisfactory high level by adjusting the number of times the solution is passed through the membrane, the above membrane tested is very advantageous for execution on an industrial scale.

TABLE 1

(Compositions of reaction mixture and aqueous solution prepared therefrom)

| | |
|---|---|
| Sucrose fatty acid ester (stearate) | 42.0 kg |
| Unreacted sucrose | 47.0 kg |
| Catalyst (K$_2$CO$_3$) | 0.5 kg |
| Unreacted fatty acid methyl ester (methyl stearate) | 1.5 kg |
| Soap (potassium stearate) | 3.0 kg |
| Fatty acid (stearic acid) | 1.0 kg |
| Volatile component (dimethylsulfoxide) | 5.0 kg |
| Water | 2,000.0 kg |
| Total (aqueous solution) | 2,100.0 kg |

Like this, by utilizing ultrafiltration membranes, it is possible to remove the unreacted sucrose, salt derived from the catalyst, and volatile component with water simultaneously and easily on an industrial scale. Thus, according to the present invention, the unreacted sucrose and the above impurities can be easily and efficiently separated from the sucrose fatty acid ester, without using organic solvents.

The ternary aqueous solution containing the unreacted sucrose, salt and volatile component which have been separated by ultrafiltration can be concentrated by general devices, and after passing through suitable steps for dehydration, concentration, etc., it can be recovered and utilized again as a raw material for the preparation of sucrose fatty acid esters.

The remaining portion which has not passed through the filtration membrane, namely sucrose fatty acid ester, unreacted fatty acid methyl ester, soap and fatty acid, is in the form of an aqueous solution. The aqueous solution is usually composed of about 1–4% by weight of solids and about 99–96% by weight of water. It may be subjected to concentration, washing and other purification operations.

If the solid concentration is very low, a great energy cost is required in concentrating the aqueous solution treated by the ultrafiltration. It has now been found that removal of water can be achieved at a very low cost by utilizing a reverse osmosis membrane, thus a powder of a sucrose fatty acid ester can be economically obtained.

Accordingly, in another aspect of the present invention, a powdery sucrose fatty acid ester is prepared from the sucrose ester-containing portion obtained by adjusting the reaction mixture in the sucrose ester production to a neutral pH region, dissolving the reaction mixture in water at an adequate temperature to give an aqueous solution having a predetermined concentration, and bringing the aqueous solution into contact with a ultrafiltration membrane under pressure, thereby separating the unreacted sucrose, salt derived from catalyst and volatile component. The sucrose ester-containing portion, namely an aqueous solution containing sucrose fatty acid ester, unreacted fatty acid methyl ester, soap and fatty acid, is brought into contact with a reverse osmosis membrane under pressure to give a slurry having an adequate concentration. The concentrated solution or slurry may be further concentrated by evaporation, as occasion demands. The slurry is then subjected to spray drying.

The membrane used in reverse osmosis should have the following properties.

(1) Only water in the solution to be treated is permeable into the membrane.

(2) The membrane is not deteriorated by propagation of microorganisms.

(3) The membrane is resistant to heat and alkali.

(4) The membrane has an excellent water removal ability.

(5) The membrane has a long working life.

In particular, a composite membrane having a fractionation molecular weight of 60 wherein a polyether membrane is reinforced by a polysulfone support, is suitable for the reverse osmosis in the present invention. Such a membrane is commercially available, and for example, a membrane "PEC 1000" sold by Toray Engineering Kabushiki Kaisha is useful.

The aqueous solution to be treated is brought into contact with the membrane under pressure at a pH of 6.2 to 8.2 and at a temperature of 40° to 60° C. When the pH of the solution is less than 6.2, the sucrose fatty acid ester deposits and chokes up the fine pores of the membrane, and accordingly permeation of water becomes impossible. When the pH of the solution exceeds 8.2, fatal hydrolysis of the sucrose ester occurs. Also, when the temperature of the aqueous solution to be treated is lower than 40° C., the velocity that water molecules pass through pores of the reverse osmosis membrane suddenly drops. On the other hand, if the temperature is higher than 60° C., it is apprehended that the sucrose ester may be hydrolyzed when subjected to reverse osmosis for a long time and, therefore, the pH over 8.2 should be avoided.

The pressure to be applied as the actuation force for reverse osmosis is preferably from 50 to 65 kg/cm$^2$G from the industrial point of view. Under this condition, the water removal velocity of about 0.06 to about 0.6 kg/minute per 1 m$^2$ of the membrane is achieved. It is sufficiently high level for the treatment on an industrial scale.

When the aqueous solution is treated under the above-mentioned conditions, the concentrated liquid usually has a water content of 60 to 96% by weight and a solid content of 40 to 4% by weight. The treated liquid which is in the form of solution or slurry may be further concentrated to a higher solid concentration by other methods, e.g. evaporation under reduced pressure. However, it should be avoided to concentrate to such an extent as making spray drying in the next step difficult.

The concentrated liquid containing 60 to 96% by weight of water which is in the state of a sort of slurry, is then dehydrated and dried. The present inventors have found that spray drying is particularly suitable for dehydration and drying of the sucrose ester slurry.

The dehydration and drying may be conducted by other known methods or devices, e.g. a conventional vacuum dryer such as a channel agitated dryer. However, these means are disadvatageous. For example, it is known from Japanese Patent Publication Kokoku No. 37-9966 that the dehydration and drying of an aqueous solution of the sucrose ester by a usual agitated vacuum dryer is difficult because of a high viscosity of the solution and is obliged to conduct at a high temperature for a long time, and consequently it causes undesirable phenomena such as rise of acid value resulting from decomposition of sucrose ester, marked coloration and caramel formation. Also, in case of a flash dryer wherein a slurry is continuously heated, fed to a vacuum chamber and released, difficulty is encountered when a sufficient drying is desired because of a large latent heat of water (over 500 kcal/kg). Even if these difficulties are overcome, the sucrose ester dehydrated and dried under vacuum is in the molten state and, therefore, it requires a pulverization step after taking out of the drier and cooling to less than the melting point to solidify, for instance, by blowing a cold air. That is to say, since the vacuum drying requires many steps such as:

(1) dehydration and drying of slurry under vacuum,
(2) withdrawal of the molten sucrose ester from a drier under vacuum,
(3) cooling for solidification of the molten mass, and
(4) pulverization of the solidified sucrose ester, it is not desirable from the economical point of view and moreover accompanies a risk of dust explosion in the pulverization step.

The dehydration and drying means for sucrose ester slurry by the spray drying involved in the present invention can eliminate the defects of the abovementioned drying means.

In the present invention, the slurry is continuously fed to a spray drying tower by a pump, and dispersed in the form of mist through a nozzle or a rotary disk, preferably through the latter. Since the surface area of water evaporation is made extremely large by spray drying, dehydration and drying can be completed in several seconds after spraying.

The slurry fed to the spray drying tower is kept at a temperature of 40° to 80° C., preferably 40° to 60° C. in consideration of quality. In case of spraying the slurry by means of a rotary disk, the number of rotations thereof is from 15,000 to 24,000 r.p.m. when the diameter of the disk is from 5 to 10 cm.

The hot air passed through the tower should have a heat energy sufficient to evaporate water included in the slurry, and accordingly when the temperature of the air is low, a large quantity of air is required as a matter of course. The temperature of the air can be selected from a range of 10° to 100° C., but for avoiding the deterioration in quality of the sucrose ester product the temperature of the air is preferably selected from a range of 60° to 80° C.

The humidity of the air passed is also important as well a the temperature, and it is economical that the absolute humidity of the air is from 0.01 to 0.04 kg water/kg dry air.

The parameters such as volume, diameter and height of the spray drying tower is determined on the basis of the above-mentioned spraying conditions. Under appropriate conditions, powder of the sucrose fatty acid ester having a water content of not more than 5% by weight can be continuously taken out from the lower part of the tower.

Like this, according to the present invention, a powder of purified sucrose fatty acid esters can be economically produced without using organic solvents from the crude reaction mixture obtained by the reaction of sucrose and a fatty acid methyl ester.

The present invention is more specifically described and explained by means of the following Examples in which all % are by weight unless otherwise noted. It is to be understood that the present invention is not limited to these Examples.

EXAMPLE 1

To a mixture of methyl stearate and sucrose in a molar ratio of 1:2 were added 3.0% of $K_2CO_3$ and 400% of dimethylsulfoxide respectively based on the solid matter. After thoroughly dehydrating the mixture, the reaction was carried out under a vacuum of 30 Torrs for 7 hours with vigorously stirring. A large portion of dimethylsulfoxide was then distilled away under reduced pressure to give a reaction mixture having the composition shown in Table 2.

TABLE 2

| Ingredients | Amount (%) |
| --- | --- |
| Sucrose fatty acid ester (monoester content: 72%) | 34.3 |
| Unreacted sucrose | 31.3 |
| Unreacted methyl stearate | 1.6 |
| Stearic acid | 1.3 |
| $K_2CO_3$ | 2.3 |
| Potassium stearate | 3.2 |
| Volatile component (dimethylsulfoxide) | 26.0 |
| Total | 100.0 |

After neutralizing 95 kg of the above reaction mixture to pH 7.5 with acetic acid, 2,700 kg of deionized water was added to the mixture, and it was stirred at 50° C. for 60 minutes for dissolution. The obtained aqueous solution had a pH of 7.3.

The aqueous solution was fed to a spiral type 4 inch cylindrical pressure filtration unit of membrane area 8 m$^2$ equipped with a ultrafiltration membrane having a fractionation molecular weight of 5,000 (commercially available under the trade mark "TERP-E-5" from Toray Engineering Kabushiki Kaisha) under the following conditions.

Temperature: 53.0° to 53.5° C.
Pressure: 6.0 to 7.2 kg/cm²G
Discharge velocity of filtrate: 2.5 to 4.6 kg/8 m².min.
Circulation velocity inside the membrane: 14.7 to 16.2 kg/8 m².min.

After 14 hours from the start of feeding, the dissolved sucrose in the filtrate discharged through the filtration membrane was measured by a refractometer and was found that 90.1% of the unreacted sucrose included in the original reaction mixture was eluted into the filtrate. In contrary, the amount of the sucrose ester leaked into the filtrate was only 0.2% of the sucrose ester included in the reaction mixture. Also, the amount of dimethylsulfoxide was measured by gas chromatography and found that 91.2% of dimethylsulfoxide included in the reaction mixture was removed into the filtrate. Further, 93.2% of potassium carbonate (catalyst) included in the reaction mixture was removed as potassium acetate derived from the catalyst.

EXAMPLE 2

Sucrose was reacted with methyl stearate in the presence of a fatty acid salt (soap) and a catalyst, and the reaction mixture having the composition shown in Table 3 was obtained.

TABLE 3

| Ingredients | Amount (%) |
| --- | --- |
| Sucrose fatty acid ester (monoester content: 52%) | 46.3 |
| Unreacted sucrose | 22.1 |
| Unreacted methyl stearate | 2.5 |
| Sodium stearate | 26.4 |
| Stearic acid | 1.5 |
| Catalyst (potassium carbonate) | 1.2 |
| Total | 100.0 |

After neutralizing 72.0 kg of the reaction mixture to pH 7.1 with hydrochloric acid, 1,400 kg of deionized water was added to the mixture and it was stirred at 50° C. for 70 minutes for dissolution.

The obtained aqueous solution was fed to a spiral type 4 inch cylindrical pressure filtration unit of membrane area 8 m² equipped with a ultrafiltration membrane having a fractionation molecular weight of 100,000 (commercially available under the trade mark "TERP-HF-100" from Toray Engineering Kabushiki Kaisha) under the following conditions.
Temperature: 52.3° to 54.0° C.
Pressure: 4.6 to 6.3 kg/cm²G
Discharge velocity of filtrate: 2.9 to 5.6 kg/8 m².min.
Circulation velocity inside membrane: 17.2 to 19.3 kg/8 m².min.

After 15 hours from start of feeding, the components in the filtrate which had passed through the membrane were analyzed, and it was found that the sucrose ester, sucrose and potassium acetate derived from the catalyst by neutralization were transferred into the filtrate in amounts of 0.7%, 91.2% and 92.6% of those included in the original reaction mixture.

EXAMPLE 3

The procedure of Example 1 was repeated except that 95 kg of the reaction mixture was neutralized to pH 7.5 with acetic acid and then dissolved in 2,700 kg of deionized water, and the thus obtained aqueous solution was subjected to the ultrafiltration for 14 hours.

The results were similar to those obtained in Example 1.

The amount of the concentrate was about 290 kg, and the amount of the filtrate was about 2,490 kg.

To 290 kg of the concentrate was added 2,500 kg of deionized water, and it was stirred at 50° C. for 60 minutes for dissolusion. After adjusting to pH 7.4, the aqueous solution was subjected to ultrafiltration again under approximately the same condition as above. After 14 hours, 846 kg of a concentrate having the following composition was obtained.

| Ingredients | Amount (%) |
| --- | --- |
| Sucrose stearate | 3.73 |
| Unreacted sucrose | 0.11 |
| Unreacted methyl stearate | 0.17 |
| Stearic acid | 0.14 |
| Potassium stearate | 0.34 |
| Volatile component (dimethylsulfoxide) | 0.1 |
| Potassium acetate | 0.01 |
| Water | 95.4 |
| Total | 100.0 |

From the above results, it is found that at least 98% of the objective sucrose stearate was recovered, and in addition, 97% of the unreacted sucrose, 97% of dimethylsulfoxide and 97% of potassium acetate derived from the catalyst ($K_2CO_3$) were removed. The unreacted methyl stearate, stearic acid and potassium stearate were not removed because of included in sucrose stearate micelles.

Then, 846 kg of the above concentrate was fed to a spiral type cylindrical unit of membrane area 8 m² equipped with a reverse osmosis membrane having a fractionation molecular weight of 60 (commercially available under the trade mark "PE1000" sold by Toray Engineering Kabushiki Kaisha) at 50° C. under the following operation conditions.
Feeding pressure: 57 to 59 kg/cm²G
Discharge velocity of filtrate discharged through the reverse osmosis membrane: 0.5 to 1.9 kg/8 m².min.
Circulation velocity inside the membrane: 13.5 to 18.5 kg/8 m².min.

After 8 hours, the amount of the concentrate was 413 kg (amount of filtrate calculated: 433 kg). The concentrate had the following composition.

| Ingredients | Amount (%) |
| --- | --- |
| Sucrose stearate | 7.66 |
| Unreacted sucrose | 0.22 |
| Unreacted methyl stearate | 0.34 |
| Stearic acid | 0.28 |
| Potassium stearate | 0.68 |
| Volatile component (dimethylsulfoxide) | 0.2 |
| Potassium acetate | 0.02 |
| Water | 90.6 |
| Total | 100.0 |

Like this, it was found that about half of only water included in the concentrate could be removed through the reverse osmosis membrane.

The concentrate obtained by the reverse osmosis was kept at 50° C. and fed to a spray drying tower equipped with a rotary disk. The conditions of spray drying were as follows:
Diameter of spray drying tower: 2.0 m
True cylindrical portion: 1.5 m
Fed air: 360 N m³/hour
Diameter of rotary disk: 10 cm
Number of rotations of the disk: 20,000 r.p.m.

Temperature of air at inlet: 70° C.
Absolute humidity of air at inlet: 0.023 kg water/kg dry air
Feeding velocity of concentrate: 1.1 to 1.3 kg/hour The powdery sucrose ester obtained from the lower part of the spray drying tower had an acid value of 5.1, no coloration due to heating, a water content of 1.75%, a bulk specific gravity of 0.43 and a good flowability.

The drying was continued stably for about 2 hours, and there was no troubles such as sticking to the inner surface of the wall of the drying tower. Also, the monoester content of the obtained sucrose ester powder was 72%, thus there was no change compared with that of the sucrose ester before drying.

EXAMPLE 4

The procedure of Example 2 was repeated except that 72.0 kg of the reaction mixture was neutralized to pH 7.1 with acetic acid and then dissolved in 2,800 kg of deionized water, and the thus obtained aqueous solution was subjected to the ultrafiltration for 14 hours.

The results were similar to those obtained in Example 2. That is to say, the amount of the sucrose ester leaked into the filtrate was 0.7% of the initial amount, and removal of 91.2% of sucrose and 92.6% of potassium acetate derived from the catalyst was achieved.

The amount of the concentrate was about 470 kg, and the amount of the filtrate was about 2,400 kg.

In 470 kg of the concentrate was added 2,800 kg of deionized water, and it was dissolved again in water. After adjusting to pH 7.3, the aqueous solution was subjected to ultrafiltration again under approximately the same condition as above at 50° C. After about 13 hours, 400 kg of a concentrate having the following composition was obtained (the amount of filtrate: 2,870 kg).

| Ingredients | Amounts (%) |
| --- | --- |
| Sucrose stearate | 8.25 |
| Unreacted sucrose | 0.08 |
| Unreacted methyl stearate | 0.45 |
| Sodium stearate | 4.63 |
| Stearic acid | 0.25 |
| Water | 86.34 |
| Total | 100.0 |

From the above results, it is found that approximately the whole amount of the objective sucrose stearate was recovered, and in addition, 98% of the unreacted sucrose and the whole amount of potassium acetate derived from the catalyst ($K_2CO_3$) were removed. Almost whole amounts of the unreacted methyl stearate, sodium stearate and stearic acid remain in the concentrate.

The above concentrate was treated by reverse osmosis and spray-dried in the same manner as in Example 3 to give a sucrose stearate powder. The powder product had a water content of 1.56% and an acid value of 4.1. There is no change in the acid value between before and after the spray drying. Also, marked coloration and other results showing thermal deterioration were not observed. Further, there is no change in the amount of monoester in the sucrose ester, and the monoester content was 52%.

COMPARATIVE EXAMPLE 1

For conducting dehydration and drying, 5.0 kg of the concentrate obtained by ultrafiltration in Example 3 was heated at 90° C. under a vacuum of 5 Torrs while kneading in a 10 liter kneader.

After 130 minutes, the water content of the dried matter in the kneader was measured. It was as high as 6.2%. Also, the acid value was 8.3, and it was twice that before drying. Further, the dried matter was colored due to thermal deterioration, thus change into caramel was observed. Moreover, the monoester content in the sucrose ester decreased to 61.3%.

COMPARATIVE EXAMPLE 2

For conducting dehydration and drying, 5.0 kg of the concentrate obtained in Example 4 was heated at 95° C. under a vacuum of 5 Torrs while kneading in a 10 liter kneader.

After 130 minutes, the water content of the dried matter in the kneader was measured. The water content was as high as 8.1%. Also, the acid value increased to 9.1. The dried matter is markedly colored due to thermal deterioration. Moreover, the monoester content in the sucrose ester decreased to 43.3%.

As described above, the present invention has the following advantages.

(1) The unreacted sucrose can be removed from the reaction mixture together with remaining catalyst, salt derived from the catalyst, volatile component and other impurities without using organic solvents conventionally used for the purification, thus purification of sucrose fatty acid ester is possible with use of inexpensive water.

(2) Since the drying of sucrose fatty acid esters can be made in a short time under ordinary pressure, thermal deterioration of the product does not occur during the drying.

(3) Since organic solvent are not used in the purification, an expensive electric device for explosion prevention is not required, and there is no risk of explosion, fire and bad influence on workers.

(4) Since no organic solvents are used in the purification, the product is not contaminated with the organic solvents.

(5) Industrialization is very easy at a low cost.

What we claim is:

1. A process for treating a reaction mixture containing a sucrose fatty acid ester produced by the reaction of sucrose and a fatty acid alkyl ester in the presence of catalyst, which comprises subjecting to ultrafiltration an aqueous solution of a sucrose fatty acid ester containing the unreacted sucrose, the unreacted fatty acid alkyl ester, the catalyst, a soap, a fatty acid and a volatile component, wherein said reaction mixture is adjusted to pH in the range between 7.1 to 8.2 by adding an acid to the reaction mixture prior to addition of water.

2. The process of claim 1, wherein the membrane used for the ultrafiltration is made of a polysulfone or a polyvinylidene fluoride.

3. The process of claim 2, wherein said membrane for ultrafiltration has a fractionation molecular weight of 1,000 to 100,000.

4. The process of claim 1, wherein said aqueous solution of a sucrose fatty acid ester is prepared from the reaction mixture obtained by the reaction of sucrose and a fatty acid methyl ester by adding water to the reaction mixture in a reaction mixture/water ratio of 1:5 to 1:40 by weight.

5. The process of claim 1, wherein said aqueous solution is maintained at a temperature of 40° to 60° C.

6. The process of claim 1, wherein said ultrafiltration is a carried out under a pressure of 1.0 to 20.0 kg/cm$^2$G.

7. The process of claim 1, wherein said reaction mixture is composed of 15 to 95% by weight of a sucrose fatty acid ester, 1 to 80% by weight of the unreacted sucrose, 0.5 to 10% by weight of an unreacted fatty acid methyl ester, 0.05 to 7% by weight of $K_2CO_3$ as a catalyst, 1 to 60% by weight of soap, 0.5 to 10% by weight of a fatty acid and 0 to 50% by weight of a volatile component.

8. The process of claim 1, wherein the fatty acid residues of said fatty acid alkyl ester, soap and fatty acid are the same and have 8 to 22 carbon atoms.

9. The process of claim 1, wherein said volatile component is a member selected from the group consisting of water, dimethylsulfoxide and dimethylformamide.

10. A process for preparing a powder of a sucrose fatty acid ester which comprises subjecting an aqueous solution of a reaction mixture obtained by the reaction of sucrose and a fatty acid methyl ester in the presence of a catalyst to ultrafiltration, said reaction mixture containing the unreacted sucrose, the unreacted fatty acid methyl ester, the catalyst, a soap, a fatty acid and a volatile component, thereby separating the unreacted sucrose, a salt drived from the catalyst and the volatile component with water, bringing the remaining aqueous solution containing the sucrose fatty acid ester, the unreacted fatty acid methyl ester, the soap and the fatty acid into contact with a reverse osmosis membrane, thereby concentrating the aqueous solution, and spray drying the resulting concentrate.

11. The process of claim 10, wherein said reaction mixture is composed of 1 to 80% by weight of the unreacted sucrose, 0.5 to 10% by weight of the unreacted fatty acid methyl ester, 0.05 to 7% by weight of the catalyst as $K_2CO_3$, 1 to 60% by weight of the soap, 0.5 to 10% by weight of the fatty acid, 0 to 50% by weight of the volatile component and 15 to 95% by weight of the sucrose fatty acid ester.

12. The process of claim 10, wherein said aqueous solution of reaction mixture is prepared by adjusting the reaction mixture to pH 7.1 to 8.2 with an acid selected from the group consisting of lactic acid, acetic acid, sulfuric acid and hydrochloric acid and adding water to the reaction mixture in a reaction mixture/water ratio of 1:5 to 1:40 by weight.

13. The process of claim 10, wherein said ultrafiltration is carried out at a temperature of 40° to 60° C. under a pressure of 1 to 20 kg/cm$^2$G.

14. The process of claim 10, wherein the membrane used for said ultrafiltration is made of a polysulfone or a polyvinylidene fluoride and has a fractionation molecular weight of 1,000 to 100,000.

15. The process of claim 10, wherein said fatty acid methyl ester has a $C_8$ to $C_{22}$ fatty acid residue, said sucrose fatty acid ester has a softening point or melting point of at least 47° C., and the fatty acid residues of the soap and the fatty acid are the same as the fatty acid residue of the fatty acid methyl ester.

16. The process of claim 10, wherein said reverse osmosis membrane is made of a polyether resin and has a fractionation molecular weight of 60.

17. The process of claim 10, wherein the reverse osmosis is carried out under a pressure of 50 to 65 kg/cm$^2$G.

18. The process of claim 10, wherein the solid content of said concentrate to be spray-dried is from 4 to 40% by weight.

19. The process of claim 10, wherein said spray drying is carried out while blowing dry air having an absolute humidity of 0.008 to 0.05 kg water/kg dry air and maintained at a temperature of 10° to 100° C.

* * * * *